US007824914B2

(12) United States Patent
Ho et al.

(10) Patent No.: US 7,824,914 B2
(45) Date of Patent: Nov. 2, 2010

(54) **FLAVONOIDS-RICH TISSUES FROM *NEOMARICA GRACILIS* AND METHODS FOR CULTURING THE SAME**

(75) Inventors: Chin-Wen Ho, Taipei (TW); Tin-Hui Chu, Taipei (TW)

(73) Assignees: Tatung Company, Taipei (TW); Tatung University, Taipei (TW)

( * ) Notice: Subject to any disclaimer, the term of this patent is extended or adjusted under 35 U.S.C. 154(b) by 622 days.

(21) Appl. No.: 11/797,145

(22) Filed: May 1, 2007

(65) Prior Publication Data

US 2008/0160615 A1    Jul. 3, 2008

(30) Foreign Application Priority Data

Dec. 29, 2006    (TW)    .............................. 95149939 A

(51) Int. Cl.
*C12N 5/00*    (2006.01)
*C12N 5/02*    (2006.01)
(52) U.S. Cl. ........................ 435/410; 435/420; 435/430; 435/431; 424/773
(58) Field of Classification Search ................... 435/410
See application file for complete search history.

(56) References Cited

U.S. PATENT DOCUMENTS

2004/0176310 A1    9/2004    Wuttke et al.

OTHER PUBLICATIONS

Chu, T. "The Rhizome Tissue Multiplication, Tectorigenin and Total Flavonoid Analysis of *Neomarica gracilis* and Belamcanda chinensis by Liquid Culture," Thesis for Master of Science, Tatung University, Jul. 2006.*

Dodds et al. "Experiments in Plant Tissue Culture," Cambridge University Press, 3$^{rd}$ Edition, 1995, pp. 198, 205-207 and 240.*
Zhong et al. "Effects of plant growth regulators on cell growth and ginsenoside saponin production by suspension cultures of Panax quinquefolium," Journal of Biotechnology 45 (1996) 227-234.*
Tomoyoshi Akashi et al, "Isoflavonoid production by adventitious-root cultures of *Iris germanica* (*Iridaceae*)", Plant Biotechnology vol. 22(3), 2005, pp. 207-215.
Adbel Nasser B. Singab, "Flavonoids from *Iris spuria* (Zeal) Cultivated in Egypt", Arch Pharm Res vol. 27, No. 10, 1023-1028, 2004.
Min-Jian Qinet al., "A New Isoflavonoid from *Belamcanda chinensis* (L.) DC.", Journal of Integrative Plant Biology (Formerly Acta Botanica Sinica), vol. 47, No. 11, 2005, pp. 1404-1408.
Tin-Hui Chu; The Rhizome Tissue Multiplacation, Tectorigenin and Total Flavonoid . . . ; Thesis for Master of Science Department of Bioengineering Tatung University; Jul. 2006.
Abdel Nasser B. Singab; Flavonoids from *Iris spuria* (Zeal) Cultivated in Egypt; Arch Pharm Res; 2004; vol. 27, No. 10; pp. 1023-1028.
Min-Jian Qin; A New Isoflavonoid from *Belamcanda chinensis* (L.) DC.; Journal of Integrative Plant Biology; 2005; vol. 47; pp. 1404-1408.

* cited by examiner

*Primary Examiner*—Susan B McCormick Ewoldt
(74) *Attorney, Agent, or Firm*—Andrews Kurth LLP

(57) ABSTRACT

The present invention provides an in vitro flavonoid-rich rhizome tissue of *Neomarica gracilis*, which is obtained from a tissue culture preparation of an *N. gracilis* tissue capable of proliferating, such as a root, a leaf, a basal portion of a leaf, and/or a rhizome. The in vitro flavonoid-rich rhizome tissue of *N. gracilis* contains tectorigenin, which is distinctively different from the naturally grown rhizome of *N. gracilis* which contains no tectorigenin. The present invention further provides a method for cultivating the in vitro flavonoid-rich rhizome tissue, a method for extracting the tectorigenin from the flavonoid-rich rhizome tissue, and quantitative methods for determining the amount of tectorigenin in the in vitro flavonoid-rich rhizome tissue.

17 Claims, 6 Drawing Sheets
(4 of 6 Drawing Sheet(s) Filed in Color)

FLAVONOIDS-RICH TISSUES FROM *NEOMARICA GRACILIS* AND METHODS FOR CULTURING THE SAME

RELATED APPLICATION

This patent application claims the priority of Taiwan Patent Application No. 95149939, filed on Dec. 29, 2006, which is herein incorporated by reference.

FIELD OF THE INVENTION

This invention relates to an in vitro flavonoid-rich rhizome tissue of *Neomarica gracilis*, which is provided by a tissue culture preparation using an *N. gracilis* tissue capable of proliferating, such as a root, a leaf, a basal portion of a leaf, and/or a rhizome. The flavonoid-rich rhizome tissue of *N. gracilis* contains tectorigenin, which is distinctively different from the wild rhizome of *N. gracilis*, which contains no tectorigenin. The present invention further provides a method for cultivating the flavonoid-rich rhizome tissue in vitro, a method for extracting tectorigenin from the flavonoid-rich rhizome tissue, and quantitative methods for determining the amount of tectorigenin in the flavonoid-rich rhizome tissue.

BACKGROUND OF THE INVENTION

Phytochemicals are substances that plants naturally produce to protect themselves against bacteria, viruses, and fungi. There has been a lot of interest in phytochemicals recently because many of them have demonstrated effects on slowing the aging process and reduce the risk for cancer, heart disease, and other chronic health conditions.

More than 900 different phytochemicals have been found in plant foods, with others still to be discovered. Fruits, vegetables, whole grains, soy and nuts are all sources of these disease-fighting substances. Phytochemicals are usually related to plant pigments, so fruits and vegetables with bright colors (yellow, orange, red, blue, purple, green) contain the most.

Flavonoids are a group of phytochemicals that have long been recognized to possess anti-inflammatory, antioxidant, antiallergic, hepatoprotective, antithrombotic, antiviral, and anticarcinogenic activities. The flavonoids are typically phenolic compounds and, therefore, act as potent metal chelators and free radical scavengers. They are powerful chain-breaking antioxidants. The flavonoids display a remarkable array of biochemical and pharmacological actions, some of which suggest that certain members of this group of compounds may significantly affect the function of various mammalian cellular systems. Recent reports indicate that plant flavonoids cause the activation of bacterial (*Rhizobium*) modulation genes involved in control of nitrogen fixation, which suggests important relationships between particular flavonoids and the activation and expression of mammalian genes (See e.g., Midddledton et al., *Pharmacological Reviews*, 2000, 52:673-751).

Tectorigenin is a flavonoid. In recently years, development has been made in exploring the potential utility of tectorigenin, which has demonstrated anti-bacterial, anti-inflammatory, and cancer-preventing activities. Moreover, it has been shown that tectorigenim stimulates the production of prostaglandin, induces proliferation of macrophages, selectively modulates the activity of estrogen receptors, and controls smooth muscle contraction.

Tectorigenin is typically extracted from rhizomes of Iridaceae plants, such as *Iris germanica L., Iris pallida Lam, Iris nigricans, Iris ensata, Iris sanguinea, Iris setosa*, and *Belamacanda chinensis* (*B. chinensis*). The tectorigenin content in the rhizomes are affected by the growth conditions, such as temperature and humidity. In the case of *B. chinensis*, it usually takes 2-3 years of growth before the rhizomes can be harvested for tectorigenin extraction. Therefore, there still exists a need for methods that can effectively grow plants with a high tectorigenin content.

*Neomarica gracilis* (*N. gracilis*) is a very common horticulture plant that belongs to the Iridaceae family. It can be cultured in large scale at low cost. However, the rhizomes of naturally grown *N. gracilis* does not contain tectorigenin.

In the invention to be presented in the later sections, an in vitro rhizome of *N. gracilis* is obtained from a tissue culture preparation, which can be harvested in about 1 or 2 months. The in vitro rhizome of *N. gracilis* is rich in flavonoids and contains high content of tectorigenin, which can be used as a source for tectorigenin.

SUMMARY OF THE INVENTION

The present invention provides an in vitro flavonoid-rich tissue of *Neomarica gracilis*, which is prepared in a tissue culture environment which alters the flavonoid content of the wild-type *N. gracilis*. In particular, the flavonoid-rich tissue of the present invention contains a substantial amount of tectorigenin.

The in vitro flavonoid-rich tissue of *N. gracilis* is preferably a rhizome tissue, which is cultured from an *N. gracilis* tissue capable of proliferating. Examples of the *N. gracilis* tissue capable of proliferating include the root, the rhizome, the leaf, and a basal portion of the leaf of *N. gracilis*.

A culture medium is used in the tissue culture for preparing the flavonoid-rich tissue of *N. gracilis*. This culture medium contains (1) a plant growth regulator, (2) a salt medium, and (3) a carbohydrate. The plant growth regulator (PGR) includes cytokinins or auxins. Examples of the PGRs include, but are not limited to, indole-3-acetic acid, 2-4-dichlorophenoxyacetic acid, α-naphthaleneacetic acid, 6-benzyl-aminopurine, kinetin, and/or a mixture thereof. The plant growth regulator is preferred to be at a concentration of about 0.01 to 2.0 mg/L. The preferred salt medium is a Murashige and Skoog basic salt medium (i.e., an MS medium), which includes, but is not limited to, the following salts: sodium, potassium, nitrate, ammonium, magnesium, sulfate, calcium, iron, chloride, phosphate, manganese, iodine, borate, zinc, copper, molybdenum, cobalt, or a mixture thereof. Examples of the carbohydrate include myo-inositol, sucrose or a mixture thereof. Optionally, the culture medium can contain a vitamin, such as thiamine HCl, pyridoxine HCl, and nicotinic acid, and an ancymidol. The culture medium has a pH of about 5 to 7.

The tissue culture preparation includes a flask culture, preferably under shaking condition, a Temporary Immersion System (TIS), or a combination thereof.

The flavonoid-rich tissue from *N. gracilis* contains tectorigenin in the amount of about 2.5 to 65 mg per Kg of dry tissue weight. The total amount of flavonoids after 8 weeks of a solid tissue culture in an MS0 (i.e., an MS medium with no plant growth regulator added) is in the amount of about 10.74 mg (based on measurement using ψ-tectorigenin as a standard) per g of dry weight of the flavonoid-rich tissue.

The present invention further provides a method for obtaining the in vitro flavonoid-rich tissue from *N. gracilis*. The method includes (1) inoculating an *N. gracilis* tissue in a culture medium of the tissue culture; and (2) growing the *N. gracilis* tissue in the tissue culture for a sufficient amount of time to allow a rhizome tissue to form. The *N. gracilis* tissue is capable of cell replication, such as a root, a leaf, a basal portion of a leaf, or a rhizome.

The culture medium is preferably maintained at about 20° C. to 30° C.

The tissue culture is a flask culture, a temporary immersion system (TIS), or a combination thereof.

The sufficient amount of time for forming the flavonoid-rich rhizome tissue of *N. gracilis* is about 4 to 8 weeks.

The TIS allows the *N. gracilis* tissue to be immersed in the culture medium for about 1-3 minutes in about every 2-4 hours.

The present invention further provides a method for extracting the tectorigenin from the flavonoid-rich tissue of *N. gracilis*. The method comprises: (1) drying the in vitro flavonoid-rich tissue from *N. gracilis* to obtain a dried flavonoid-rich tissue; (2) adding an alcohol to the dried flavonoid-rich tissue to form a suspension; (3) heating the suspension to form a heated suspension; and (4) filtering the heated suspension after the heated suspension has cooled off to collect an filtrate which contains tectorigenin. The preferred method to dry the in vitro flavonoid-rich tissue is by freeze-drying. The preferred way to heat the suspension is using ultrasonic vibration while heating the suspension at about 50-70° C. for about one hour. Examples of the alcohol which can be added to the dried in vitro flavonoid-rich tissue is methanol or ethanol. Optionally, the dried in vitro flavonoid-rich tissue can be ground before the alcohol is added. The filtrate is preferred to be collected by passing the heated suspension through a Whatman® No. 1 filter.

The total amount of tectorigenin extracted from the flavoid-rich tissue of *N. gracilis* is determined by a high performance liquid chromatography (HPLC). The preferred column for HPLC is a Cosmosil® 5 C18-AR-II column. The preferred eluting solution is a solution containing methanol and water (with 0.1% acetic acid) in a volume ratio of 55:45. The amount of tectorigenin is measured at about 265 nm wavelength using an tectorigenin (Sigma® T-9165) as a standard.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
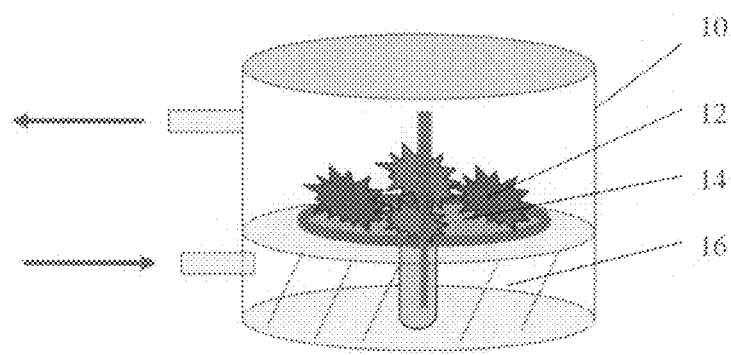
FIG. 1 is a drawing showing the Temporary Immersion System, which is one of the two tissue culture systems (the other tissue culture system is a flask culture system) used in the present invention.

One aspect of the present invention relates to a flavonoid-rich tissue of *N. gracilis*, which is obtained from a tissue culture of an *N. gracilis* tissue capable of proliferation and cell replication, such as root, leaf, the basal portion of a leaf, and rhizome. The flavonoid-rich tissue is an in vitro rhizome tissue, which is distinctively different from a wild rhizome of *N. gracilis*, by containing tectorigenin. Recent research has demonstrated that tectorigenin possesses medicinal effects on eliminating free radicals, halting the progression of tumors, and inhibiting pathological bacteria and fungus, such as *H. pylori* and mold, etc.

Tectorigenin has the chemical structure as shown below:

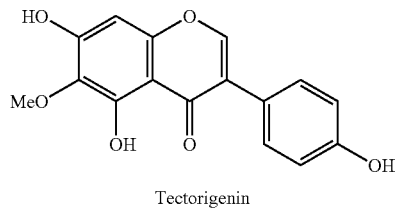

Tectorigenin

Tectorigenin is wildly found in rhizomes or roots of many Iris and legume plants, such as *Iris spuria*, *Iris carthaliniae*, and *Iris germanica*, and *Pueraria thunbergiana*. However, the amounts of tectorigenin in these plants are too low to be used of sources of tectorigenin.

The main source of tectorigenin comes from the naturally grown from the rhizomes of *Belamcanda chinensis*. However, *B. chinensis* has a slow growth rate (i.e., from seeding to harvest) of about two to three years, which makes the collection of tectorigenin difficult to achieve.

Contrary to *B. chinensis*, *N. gracilis* is a popular semi-outdoor plant, which is easy to grow and propagate. However, *N. gracilis* does not contain tectorigenin. *N. gracilis*belongs to the family of Iridaceae and the genus of *Neomarica*, which contains 16 species: *N. caerulea*, *N. capitellata*, *N. caulosa*, *N. fluminensis*, *N. gracilis*, *N. imbricata*, *N. longifolia*, *N. nitida*, *N. northiana*, *N. paradoxa*, *N. portosecurensis*, *N. rotundata*, *N. rupestris*, *N. sabini*, *N. silvestris*, and *N. varie-* gata. *N. gracilis* is native to tropical regions of western Africa, and Central and South America, with the highest concentration in Brazil. *N. gracilis* is a herbaceous perennial plant that propagate by way of a thick rhizome and new plantlets that develop from the stem where flowers once emerged.

Another aspect of the present invention relates to a method for growing an in vitro rhizome tissue of *N. gracilis* with high tectorigenin contents by tissue culture techniques for a relatively short period of time, generally between about 4 to 8 weeks and hence provides a new source of tectorigenin. The method comprises the steps of inoculating an *N. gracilis* tissue in a culture medium, and growing the *N. gracilis* tissue for a sufficient 0amount of time until the rhizome tissue is developed.

The *N. gracilis* tissue may be any tissue obtained from a naturally grown *N. gracilis* or a cultured *N. gracilis* that is capable of proliferation. Preferably, the *N. gracilis* tissue is a tissue taken from the root, rhizome, leaf, or the basal portion of the leaf of *N. gracilis*.

The culture medium comprises at least one plant growth regulator (PGR), one salt, and one carbonhydrate. PGRs cause or foster differentiation or dedifferentiation of the explanted tissues being propagated in the culture chamber. Examples of PGRs include, but are not limited to, auxins and cytokinins.

Auxin is the active ingredient in most rooting mixtures. Auxin helps the vegetative propagation of plants. On a cellular level, auxins influence cell elongation, cell division and the formation of adventitious roots. Some auxins are active at extremely low concentrations. Auxins may be used in a concentration range of 0.0001-20 mg/L, preferably 0.01-10 mg/L, more preferably 0.01-2.0 mg/L. Examples of auxins include, but are not limited to, 4-Biphenylacetic acid, 3-Chloro-4-hydroxyphenylacetic acid, 4-Hydroxyphenylacetic acid, Indole-3-acetic acid (IAA), Indole-3-propionic acid, Indole-3-butyric acid, Indole-3-acetyl-L-alanine, Indole-3-acetyl-DL-aspartic acid, Indole-3-acetyl-DL-tryptophan, Indole-3-acetyl-L-valine, 2,4-dichlorophenoxyacetic acid (2,4-D), and alpha-naphthaleneacetic acid (NAA).

Cytokinins promote cell division, stimulate shoot proliferation, activate gene expression and metabolic activity in general. At the same time, cytokinins inhibit root formation. This makes cytokinins useful in culturing plant cell tissue where strong growth without root formation is desirable. In addition, cytokinins slow the aging process in plants. Cytokinin may be used in a concentration range of 0.0001-20 mg/L, preferably 0.01-10 mg/L, more preferably 0.01-2.0 mg/L. Examples of cytokinins include, but are not limited to, N-(3-methylbut-2-enyl)-1H-purin-6-amine, 6-benzyl-aminopurine (BA), kinetin, and zeatin.

Examples of the salt include salts of inorganic acids, such as nitric acid, hydrochloric acid, phosphoric acid, sulfuric acid, boric acid, iodion acid; organic acids such as acetic acid, malonic acid, mandelic acid, oxalic acid, lactic acid, lactobionic acid, fumaric acid, maleic acid, tartaric acid, citric acid, ascorbic acid. The salt can be sodium, potassium, calcium, ammonium, iron, magnesium, manganese, zinc, copper, or cobalt salts. The culture medium may contain a mixture of salts.

In one embodiment, the culture medium includes nutrients that foster growth of an explanted plant tissue, such as, for example, the macro- and micronutrients set forth in Murashige & Skoog, *Physiol. Plant.*, 15, 473-497 (1962), which are hereinafter referred to as the "MS basal medium." The salts contained in the MS basal medium is referred to as "MS salts." MS salts used in the context of the present invention include suitable concentrations of ammonium nitrate, boric acid, calcium chloride, cobalt chloride, cupric sulfate, $Na_2$-EDTA, ferrous sulfate, magnesium sulfate, manganese sulfate, molybdic acid, potassium iodide, potassium nitrate, potassium phosphate monobasic, sodium nitrate, sodium phosphate monobasic and zinc sulfate.

The hydrocarbon can be any hydrocarbon that has nutritional value to a plant culture. Preferably, the hydrocarbon is a saccharide. More preferably, the hydrocarbon is myo-inositol, sucrose, or a mixture thereof.

The culture medium may additionally contain other components such as amino acids, vitamins, or mixtures thereof. Preferred vitamins include, but are not limited to, vitamin B1 (thiamine HCl), vitamin B6 (pyridoxine HCl), and vitamin B3 (nicotinic acid).

The culture medium is adjusted to a pH range suitable for the growth of *N. gracilis*. The pH range is preferably between 4 and 8, and more preferably between 5 and 7. In one embodiment, the culture medium includes suitable buffering agents for maintained the pH at the desired level. These agents will typically have a pKa between about 4.5 and about 5.5, and include, but are not limited to, citric acid, N-morpholino-ethansulfonic acid, potassium hydrogen phthalate, and benzoic acid.

The temperature of the culture is usually maintained at or below about 30° C., preferably within the range of about 20-30° C.

The desired growth period is 2 to 16 weeks, preferably 4-8 weeks.

In a preferred embodiment, the culture medium comprises MS salt, sucrose (30 g/L), myo-inositol (100 mg/L), 6-benzyl-aminopurine (BA) (0.5 mg/L), 2,4-dichrophenoxyacetic acid (2,4-D) (0.1 mg/L), and α-naphthaleneacetic acid (NAA) (0.84 mg/L).

In another embodiment, the *N. gracilis* tissue is cultured with constant agitation. In another embodiment, the *N. gracilis* tissue is cultured in a Temporary Immersion System (TIS). As shown in FIG. 1, a TIS nourishes and oxygenates plant cultures by intermittent immersion the plant tissue in the culture medium. Briefly, a chamber 10 holds cultures 12 on a screen 14 or in a basket. Low pressure air is pumped into the chamber 10, forcing the liquid medium 16 up and bathing the cultures 12. The air flow also oxygenates and agitates the medium 16. When the flow is turned off, pressure stops, and the medium 16 returns to the bottom of the chamber 10. Typically, all components of the TIS are autoclavable and reusable. The system may be easily automated for large scale plant tissue culture. In a preferred embodiment, the *N. gracilis* tissue is immersed by the culture medium for 1-3 minutes every 2-4 hours.

Another aspect of the present invention provides cultured *N. gracilis* tissues with high levels of tectorigenin. In one embodiment, the cultured *N. gracilis* rhizome tissues have a tectorigenin content of 2.5-65 mg/kg dry rhizome weight. The cultured *N. gracilis* rhizome tissues have a total flavonoids content of 10.741±0.311 (means±S.E.) mg/g of dry rhizome weight in solid culture containing an MS medium with no PGR added (MS0), which is measured using ψ-tectorigenin as a standard.

Another aspect of the present invention relates to a method for extracting flavonoids from *N. gracilis* tissues. The method includes the steps of drying the tissue, grinding the dried tissue, suspending the ground tissue in an alcohol, heating the suspension, and filtering the suspension to obtain extracts of flavonoids.

The plant tissue may be dried with any method, preferably by freeze-drying using a refrigerated vacuum drier. The alcohol may be any alcohol, preferably methanol, or ethanol. The alcohol is preferably heated to a temperature range of 50° C. to 70° C., and more preferably heated with shaking, vibration, or sonication. A preferred method of vibration is ultrasonic wave vibration.

The following experimental designs and result are illustrative, but not limiting the scope of the present invention. Reasonable variations, such as those occur to reasonable artisan, can be made herein without departing from the scope of the present invention. Also, in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLES

Example 1

Material and Methods

In vitro Flavonoid-rich Rhizome Tissue from *N. gracilis* (*Neomarica gracilis*)

The in vitro flavonoid-rich rhizome tissues of *N. gracilis* were cultured from Tatung University Plant Tissue Culture Lab. The rhizome tissues were subcultured every month, with an MS basal salt medium supplemented with 30 g/L sucrose, 100 mg/L myo-inositol, 0.5 mg/L BA, 0.1 mg/L 2,4-D and 0.84 mg/L NAA.

Culture Medium

The liquid culture medium comprised the MS basal salt medium (Murashige and Skoog, 1962) (Table 1) supplemented with 30 g/L sucrose, 100 mg/L myo-inositol, and various plant growth factors according to different experiments. The solid culture medium was prepared by adding 8 g/L agar to the liquid medium. The solid culture was carried out in 8×1.5×1.5 cm culture tubes (10 ml culture medium/tube) or flasks (30 ml culture medium/flask). Liquid culture was carried out in 50 ml, 100 ml or 250 ml flasks with 10 ml, 50 ml or 100 ml culture medium, respectively. The opening of the culture tubes or flasks was covered with aluminum foil.

The TIS culture used the Plantima® system from the A-Tech Bioscientific Co. Ltd. About 200 ml medium was added to each culture chamber. Plastic tubings and sterile filters membranes were placed at the gas inlet and outlet as instructed. The filter membrane was wrapped with cotton and aluminum foil, and the plastic tubings were immobilized with clamps to prevent water vapor from entering the filter. The culture chamber was covered with aluminum foil.

All the culture medium had a pH value of 5.70±0.05, and were sterilized by autoclaving at 121° C., under 1.1-1.2 $kg/cm^2$ pressure, for 15 minutes.

TABLE 1

The basal salts composition of MS (Murashige and Skoog, 1962)

| Chemical | mg/l |
|---|---|
| Macronutrients | |
| $KNO_3$ | 1900 |
| $NH_4NO_3$ | 1650 |
| $MgSO_4 \cdot 7H_2O$ | 370 |
| $CaCl_2 \cdot 2H_2O$ | 440 |
| $KH_2PO_4$ | 170 |
| Micronutrients | |
| $MnSO_4 \cdot 4H_2O$ | 22.3 |
| KI | 0.83 |
| $H_3BO_3$ | 0.2 |
| $ZnSO_4 \cdot 7H_2O$ | 8.6 |
| $CuSO_4 \cdot 5H_2O$ | 0.025 |
| $Na_2MoO_4 \cdot 2H_2O$ | 0.25 |
| $CoCl_2 \cdot 6H_2O$ | 0.025 |
| $FeSO_4 \cdot 7H_2O$ | 27.8 |
| $Na_2EDTA$ | 37.3 |

Flask Culture (1) To determine the effect of inoculum weight (expressed as a percentage of grams of fresh weight of the inoculum/100 ml of culture medium), liquid cultured *N. gracilis* rhizome tissue was inoculated to a subculture medium containing an MS basal salt, 0.5 mg/L BA, 0.1 mg/L 2,4-D and 0.84 mg/L NAA in an inoculum weight ratio of 0.5, 1, 1.5, 2, 3, 4, 5, 10 or 15% (g fresh weight (F.W.)/100 ml medium). The cultured tissue was weighted three weeks after inoculation.

(2) To determine the effect of plant growth regulators (PGR), sprouts from liquid cultured *N. gracilis* rhizome tissue were removed with a scalpel. The rhizome tissue was inoculated at an inoculum weight of 3% (g F.W./50 ml) in culture medium containing MS basic medium supplemented with PGRs as shown in Table 2. The culture medium was changed every two weeks. The cultured tissue was weighted at each medium change for a total of eight weeks.

(3) To determining the growth curve of *N. gracilis* rhizome tissue and the tectorigenin content, sprouts from liquid cultured *N. gracilis* rhizome tissues were removed with a scalpel. The rhizome tissue was inoculated at an inoculum weight (g F.W./50 ml) in culture medium containing the MS basic medium supplemented with 0.1 mg/L NAA or a mixture of 1 mg/L NAA and 1.0 mg/L 2,4-D. The tissues were weighted and analyzed for tectorigenin content every week for eight consecutive weeks.

(4) To determine ancymidol's effect on sprout formation and tectorigenin content, liquid cultured *N. gracilis* rhizome tissue was inoculated at an inoculum weight of 3% (g F.W./100 ml) to a subculture medium containing MS, 0.5 mg/L BA, 0.1 mg/L 2,4-D and 0.84 mg/L NAA. At day 7 and 14 of the culture, sterilely filtered (0.2 um) ancymidol was added to the culture medium to a final concentration of 0.5, 1.0, or 2.0 mg/L. The growth of the tissue was monitored and the tectorigenin content analyzed.

TABLE 2

Effect of plant growth regulators on N. gracilis tissue growth in flask culture

| Test sample | Mineral Comp. | Organic Substance (mg/l) | | | | | Plant Growth Regulator (mg/L) | | | | Sucrose (g/L) | pH |
|---|---|---|---|---|---|---|---|---|---|---|---|---|
| | | $V_{B1}$ | $V_{B6}$ | NA | Gly | MI | NAA | 2,4-D | Kinetin | IAA | | |
| MSO | MS | 1 | 0.5 | 0.5 | 2 | 100 | 0 | 0 | 0 | 0 | 30 | 5.7 |
| A1 | MS | 1 | 0.5 | 0.5 | 2 | 100 | | | 0.1 | 0 | 30 | 5.7 |
| A2 | MS | 1 | 0.5 | 0.5 | 2 | 100 | | | 1.0 | 0 | 30 | 5.7 |
| B1 | MS | 1 | 0.5 | 0.5 | 2 | 100 | | | 0 | 0.1 | 30 | 5.7 |
| B2 | MS | 1 | 0.5 | 0.5 | 2 | 100 | | | 0.1 | 0.1 | 30 | 5.7 |
| B3 | MS | 1 | 0.5 | 0.5 | 2 | 100 | | | 1.0 | 0.1 | 30 | 5.7 |
| C1 | MS | 1 | 0.5 | 0.5 | 2 | 100 | | | 0 | 0.5 | 30 | 5.7 |
| C2 | MS | 1 | 0.5 | 0.5 | 2 | 100 | | | 0.1 | 0.5 | 30 | 5.7 |
| C3 | MS | 1 | 0.5 | 0.5 | 2 | 100 | | | 1.0 | 0.5 | 30 | 5.7 |
| D1 | MS | 1 | 0.5 | 0.5 | 2 | 100 | | | 0 | 1.0 | 30 | 5.7 |
| D2 | MS | 1 | 0.5 | 0.5 | 2 | 100 | | | 0.1 | 1.0 | 30 | 5.7 |
| D3 | MS | 1 | 0.5 | 0.5 | 2 | 100 | | | 1.0 | 1.0 | 30 | 5.7 |
| E1 | MS | 1 | 0.5 | 0.5 | 2 | 100 | | | 0 | 2.0 | 30 | 5.7 |
| E2 | MS | 1 | 0.5 | 0.5 | 2 | 100 | | | 0.1 | 2.0 | 30 | 5.7 |
| E3 | MS | 1 | 0.5 | 0.5 | 2 | 100 | | | 1.0 | 2.0 | 30 | 5.7 |
| F1 | MS | 1 | 0.5 | 0.5 | 2 | 100 | 0 | 0.1 | | | 30 | 5.7 |
| F2 | MS | 1 | 0.5 | 0.5 | 2 | 100 | 0 | 1.0 | | | 30 | 5.7 |
| G1 | MS | 1 | 0.5 | 0.5 | 2 | 100 | 0.1 | 0 | | | 30 | 5.7 |
| G2 | MS | 1 | 0.5 | 0.5 | 2 | 100 | 0.1 | 0.1 | | | 30 | 5.7 |
| G3 | MS | 1 | 0.5 | 0.5 | 2 | 100 | 0.1 | 1.0 | | | 30 | 5.7 |
| H1 | MS | 1 | 0.5 | 0.5 | 2 | 100 | 0.5 | 0 | | | 30 | 5.7 |
| H2 | MS | 1 | 0.5 | 0.5 | 2 | 100 | 0.5 | 0.1 | | | 30 | 5.7 |
| H3 | MS | 1 | 0.5 | 0.5 | 2 | 100 | 0.5 | 1.0 | | | 30 | 5.7 |
| I1 | MS | 1 | 0.5 | 0.5 | 2 | 100 | 1.0 | 0 | | | 30 | 5.7 |
| I2 | MS | 1 | 0.5 | 0.5 | 2 | 100 | 1.0 | 0.1 | | | 30 | 5.7 |
| I3 | MS | 1 | 0.5 | 0.5 | 2 | 100 | 1.0 | 1.0 | | | 30 | 5.7 |
| J1 | MS | 1 | 0.5 | 0.5 | 2 | 100 | 2.0 | 0 | | | 30 | 5.7 |
| J2 | MS | 1 | 0.5 | 0.5 | 2 | 100 | 2.0 | 0.1 | | | 30 | 5.7 |
| J3 | MS | 1 | 0.5 | 0.5 | 2 | 100 | 2.0 | 1.0 | | | 30 | 5.7 |

TIS Culture

TIS Plantima® culture system was purchased from A-Tect Bioscientific Co., Ltd., in Taipei, Taiwan).

(1) To determine the effect of the inoculation weight on tissue growth, the TIS culture chamber was divided into four areas. Liquid cultured N. gracilis rhizome tissue was inoculated at 1.5, 3, 6 and 9 g in each area. The culture medium was an MS medium supplemented with PGR as described in samples T12, T17 and T18 of Table 3. The tissues were cultured under conditions detailed in the Plantima® user's manual and immersed for two minutes every three hours. The cultured tissue was weighted and the medium replaced every ten days.

(2) To determine the effect of PLRs on the grows of N. gracilis and the tectorigenin content influence, ten pieces of liquid cultured N. gracilis rhizome tissue were inoculated in culture media containing MS and PGRs described in samples MS0, TI3, TI4, TI5 and TI6 of Table 3. The culture media were replaced on week 2 and the tissues were harvested on week 4 and analyzed for tectorigenin content.

TABLE 3

Effect of plant growth regulators on N. gracilis tissue growth in TIS culture

| Test sample | Mineral Comp. | Organic Substance (mg/L) | | | | | Plant Growth Regulator (mg/L) | | | | Sucrose (g/L) | pH |
|---|---|---|---|---|---|---|---|---|---|---|---|---|
| | | $V_{B1}$ | $V_{B6}$ | NA | Gly | MI | BA | NAA | 2,4-D | Kinetin | | |
| MSO | MS | 1 | 0.5 | 0.5 | 2 | 100 | 0 | 0 | 0 | 0 | 30 | 5.7 |
| TI2 | MS | 1 | 0.5 | 0.5 | 2 | 100 | 0 | 0 | 0 | 1.0 | 30 | 5.7 |
| TI3 | MS | 1 | 0.5 | 0.5 | 2 | 100 | 0 | 0.1 | 0 | 0 | 30 | 5.7 |
| TI4 | MS | 1 | 0.5 | 0.5 | 2 | 100 | 0 | 0.5 | 0 | 0 | 30 | 5.7 |
| TI5 | MS | 1 | 0.5 | 0.5 | 2 | 100 | 0.5 | 0.84 | 0.1 | 0 | 30 | 5.7 |
| TI6 | MS | 1 | 0.5 | 0.5 | 2 | 100 | 0 | 1.0 | 0.1 | 0 | 30 | 5.7 |
| TI7 | MS | 1 | 0.5 | 0.5 | 2 | 100 | 0 | 1.0 | 1.0 | 0 | 30 | 5.7 |
| TI8 | MS | 1 | 0.5 | 0.5 | 2 | 100 | 0 | 2.0 | 1.0 | 0 | 30 | 5.7 |

Extraction of Tectoriaenin and Total Flavonoid

N. gracilis rhizome tissue was frozen at −80° C. for 10 hours, dried in a refrigerated vacuum drier (VirTis Freezemobile 12XL) overnight, and grinded. 0.5 g of dried and grinded tissue was suspended in adequate amount of methanol in a 10 ml flask, incubatedgrinded tissue was suspended in adequate amount of methanol in a 10 ml flask, incubated at 60° C. with ultrasonic vibration for 1 hour, and cooled. Methanol was then added to the suspension to a final volume of 10 ml. The suspension was filtered with Whatman No. 1 filter paper. The filtered solution was sealed in brown sample vials and placed in cold room for future experiments.

Prior to the determination of tectorigenin content, tectorigenin standard (Sigama T-9165, ψ-tectorigenin) solution and the samples were filtered through a 0.45 um filter. The filtered samples were sealed in 2 ml brown HPLC vials for further analysis.

Measurement of Total Flavonoid

Total flavonoid was measured according to Lee et al., *J. Agric. Food Chem.* (2003) 51: 7292-7295. Briefly, 4 ml of deionized water and 0.3 ml of 5% $NaNO_2$ were added to about 0.5 ml of *N. Gracilis* extract to form a sample mixture and allowed for reaction for about 5 minutes. About 0.3 ml of 10% $AlCl_3$ was then added to the reacted sample mixture and allowed for further reaction for an additional 5 minutes under thorough shaking. This was followed by the addition of 2 ml of 1 N NaOH and 2.9 ml of deionized water to the further reacted sample mixture. The total flavonoid in the resulting reacted sample mixture was then determined by measuring the absorbance at 510 nm wavelength with an UV spectrophotometer (Ultrospec 2000, Pharmacia Biotech), and comparing the data with the standard curve using ψ-tectorigenin as a standard.

Measurement of Tectorigenin by HPLC

The tectorigenin content of the tissue extract was determined by HPLC analysis using a Cosmosil 5 C18-AR-II column (5 μm, 4.6×250 mm), a Lichrospher® 100 RP-18e Guard column (45×4.6 mm, 5 μm, Merck), a Degasser (ERC-3415α) Pump, a Waters 600E Autosampler and Injector (Schambeck SGD GmbH S5200), a Waters TM 486 UV/VIS Detector, and an Integrator (SISC Xunhua Ltd.). The analysis was performed using a methanol:$H_2O$ (0.1% Acetic acid) ratio of 55:45, a flowrate of 0.8 ml/min, and a detection wavelength of 265 nm. The tectorigenin peak of the standard appeared at about 13 min appear.

Statistic Analysis

All the measurements were repeated for three times. The experimental data were analyzed using Duncan's multiple range test with 5% significance level (Duncan D. B. 1955, Biometrics, 11:1-42).

Morphology Observation and Photograph

Morphology observations were made under a dissecting microscope (Olympus SZ-ET). Photographic records were made using a digit camera (Nikon coolpix 8700).

Example 2

Effect of Inoculum Weight on Tissue Growth in Flask Culture

Figure 2:
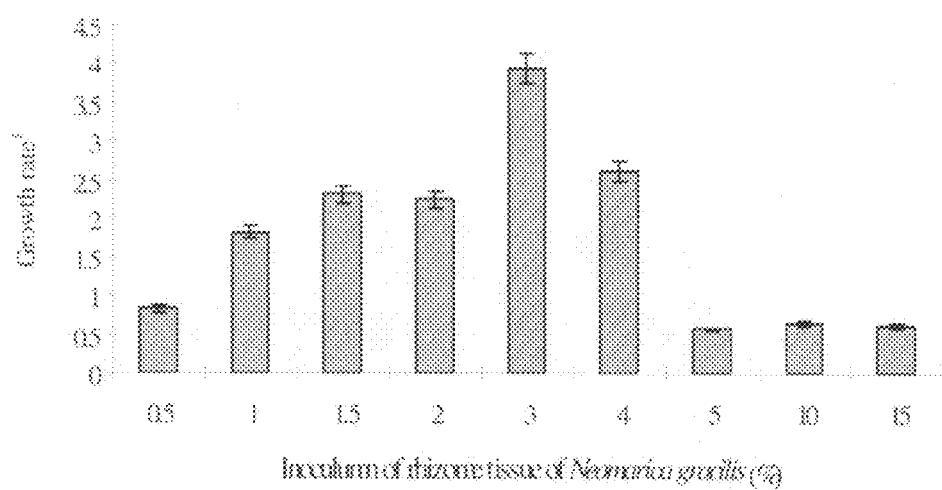
FIG. 2 is a diagram showing the effect of inoculum weight ratio on the growth rate of the in vitro flavonoid-rich rhizome tissue of *N. gracilus* in a flask culture. Data were collected from the rhizome tissue cultured in an MS medium (Murashige and Skoog medium) containing 0.5 mg/L of 6-benzylaminopurine (BA), 0.1 mg/L of 2,4-dichlorophenoxyacetic acid (2,4-D), and 0.84 mg/L of α-naphthaleneacetic acid (NAA) for 3 weeks. Each data point represents an average of 3 replications and the error bars represent the standard errors of the means.

Liquid cultured *N. gracilis* rhizome tissue was inoculated to a subculture medium containing MS, 0.5 mg/L BA, 0.1 mg/l 2,4-D and 0.84 mg/L NAA at an inoculum weight of 0.5, 1, 1.5, 2, 3, 4, 5, 10 or 15% (g fresh weight (F.W.)/100 ml medium). As shown in FIG. 2, the inoculum weight of 3% (g fresh weight (F.W.)/100 ml medium) resulted the highest growth rate, i.e., about a four fold increase of the fresh weight ((fold increase of the fresh weight=final fresh weight−initial fresh weight)/initial fresh weight). The weight gain diminished when inoculum weight is greater than 4%, probably due to the limited space and nutrition supply in the flask.

Example 3

Effect of PGR on Tissue Growth and Tectorigenin Content in Flask Culture

Figure 3:
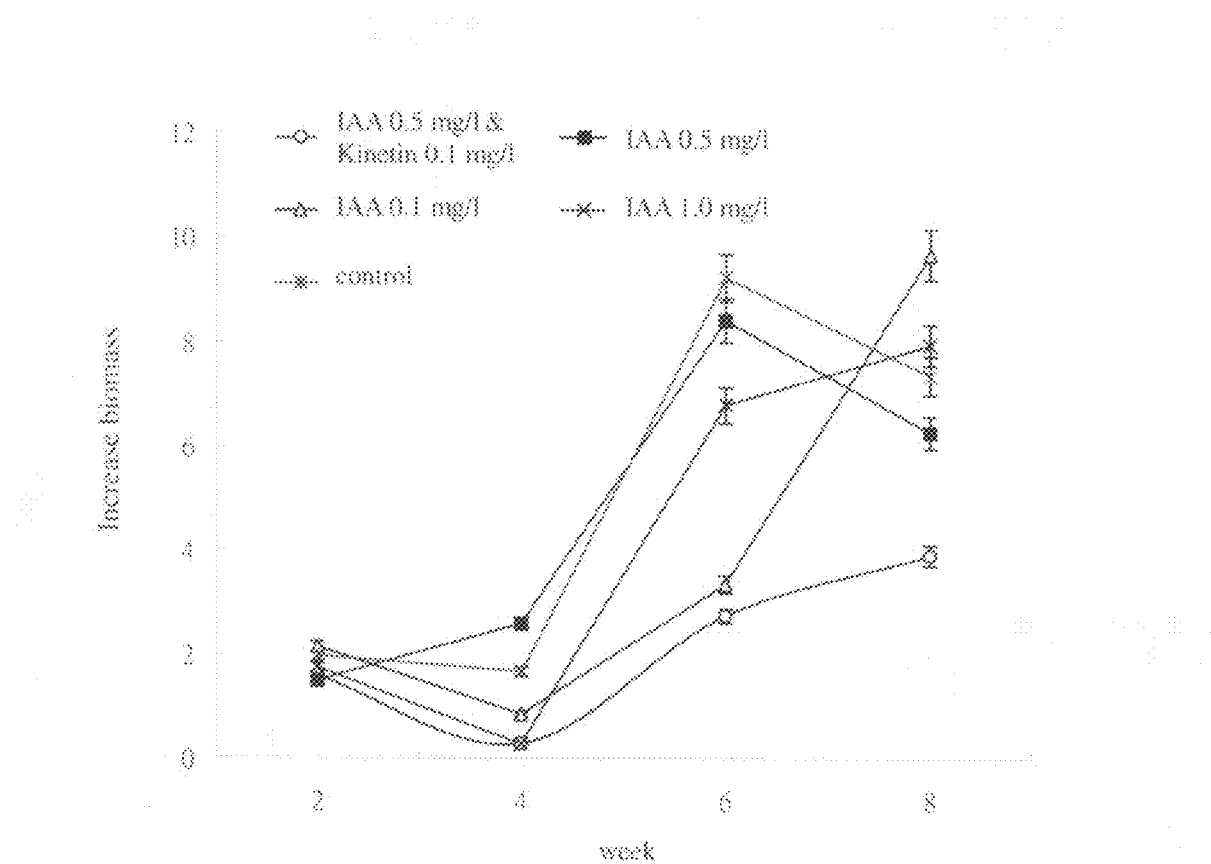
FIG. 3 is a diagram showing the effect of indole-3-acetic acid (IAA) and Kinetin on increase of the biomass in the in vitro flavonoid-rich rhizome tissue of *Neomarica gracilis*, where the rhizome tissue is obtained from a flask culture. Each data point represents an average of 3 replications and error bars represent the standard errors of the means. The biomass increase=current fresh weight–the fresh weight of 2 weeks ago.

*N. gracilis* rhizome tissue was inoculated at an inoculum weight of 3% (g F.W./100 ml) in culture medium containing MS supplemented with various amount of PGRs (Table 2). The culture medium was changed and the fresh weight of the tissues was measured every two weeks. Significant increases in fresh weight were observed during 6-8 weeks of culture (FIG. 3).

Among the 15 Kinetin/IAA combinations listed in Table 2, only 4 combinations (i.e., B1, C1, C2, and D1) resulted in significant increases in tectorigenin content. Among the 4 combinations that led to increased tectorigenin content, the combination of 0.5 mg/L IAA/0 mg/L Kinetin provided the highest tectorigenin content of 37.6±4.9 mg/kg D.W. (Table 4). It appears that adding kinetin to the culture medium did not result in any increase in the tectorigenin content.

TABLE 4

Effects of IAA and Kinetin on dry weight, and tectorigenin content in the rhizome tissue of *Neomarica gracilis*.

| Plant growth regulators (mg/L) | | Dry weight (g)[1] | Tectorigenin (mg/kg D.W.)[1] |
|---|---|---|---|
| IAA | Kinetin | | |
| 0 | 0 | 1.08 ± 0.16 bc[2] | 3.0 ± 0.24 d[2] |
| 0.5 | 0.1 | 0.93 ± 0.06 c | 37.0 ± 1.2 a |
| 0.1 | 0 | 1.26 ± 0.22 b | 11.8 ± 8.4 b |
| 0.5 | 0 | 1.02 ± 0.11 bc | 37.6 ± 4.9 a |
| 1 | 0 | 1.70 ± 0.08 a | 29.0 ± 0.29 c |

[1]Data were collected after 8 weeks culture, and values are means of 3 replicates ± S.E.
[2]Means within a column followed by the same (a to d) letters are not significantly different by Duncan's multiple range test (P > 0.05).

Increased tectorigenin content was also found in all tissues cultured in the presence of 2,4-D and NAA, as well as in some tissues cultured with NAA only (Table 5). The highest tectorigenin contents were found in tissues cultured in the presence of 1.0 mg/L NAA and 0.1 mg/L 2,4-D (60.9±0.67 mg/kg D.W.), 0.5 mg/L NAA only (58.9±0.23 mg/kg D.W.), and 0.1 mg/L NAA only (55.5±0.67 mg/kg D.W.). When NAA is used alone, an increase of the NAA concentration led to decreased dry weight. The highest dry weight was obtained with a NAA concentration of 0.1 mg/L (Table 5).

TABLE 5

Effects of NAA and 2,4-D on dry weight and tectorigenin content in rhizome tissue of *Neomarica gracilis*.

| Plant growth regulators (mg/l) | | | |
|---|---|---|---|
| 2,4-D | NAA | Dry weight (g)[1] | Tectorigenin (mg/kg D.W.)[1] |
| 0 | 0 | 1.17 ± 0.02 ab[2] | 8.2 ± 0.42 e[2] |
| 0 | 0.1 | 1.39 ± 0.32 a | 55.5 ± 0.67 ab |
| 0 | 0.5 | 1.03 ± 0.31 bc | 58.9 ± 0.23 ab |
| 0 | 1.0 | 1.05 ± 0.20 bc | 49.0 ± 0.81 bc |
| 0 | 2.0 | 0.75 ± 0.02 cd | 9.4 ± 0.22 e |
| 0.1 | 0 | 0.92 ± 0.15 bc | 38.9 ± 1.17 cd |
| 0.1 | 0.1 | 1.06 ± 0.03 bc | 49.5 ± 1.21 bc |
| 0.1 | 0.5 | 0.92 ± 0.13 bc | 40.1 ± 0.55 cd |
| 0.1 | 1.0 | 0.95 ± 0.01 bc | 60.9 ± 0.67 a |
| 0.1 | 2.0 | 0.93 ± 0.02 bc | 14.5 ± 0.67 e |
| 1.0 | 0 | 1.17 ± 0.21 ab | 36.7 ± 0.33 cd |
| 1.0 | 0.1 | 1.39 ± 0.54 a | 35.3 ± 0.23 d |

TABLE 5-continued

Effects of NAA and 2,4-D on dry weight and tectorigenin content in rhizome tissue of *Neomarica gracilis*.
Plant growth regulators (mg/l)

| 2,4-D | NAA | Dry weight (g)[1] | Tectorigenin (mg/kg D.W.)[1] |
|---|---|---|---|
| 1.0 | 0.5 | 1.03 ± 0.12 bc | 33.4 ± 0.16 d |
| 1.0 | 1.0 | 1.05 ± 0.10 bc | 16.5 ± 0.80 e |
| 1.0 | 2.0 | 0.75 ± 0.03 cd | 38.0 ± 1.13 cd |

[1]Data were collected after 8 weeks culture, and values are means of 3 replicates ± S.E.
[2]Means within a column followed by the same (a to e) letters are not significantly different by Duncan's multiple range test (P > 0.05).

Example 4

Growth Rate of *N. gracilis* and the Tectorigenin Content during Growth

Rhizome tissue was inoculated at an inoculum weight of 3% (g F.W./50 ml) in culture medium containing MS basic medium supplemented with 0.1 mg/L NAA or a mixture of 1 mg/L NAA and 1.0 mg/l 2,4-D. The tissues were weighted and analyzed for tectorigenin content every week for eight consecutive weeks.

Figure 4:
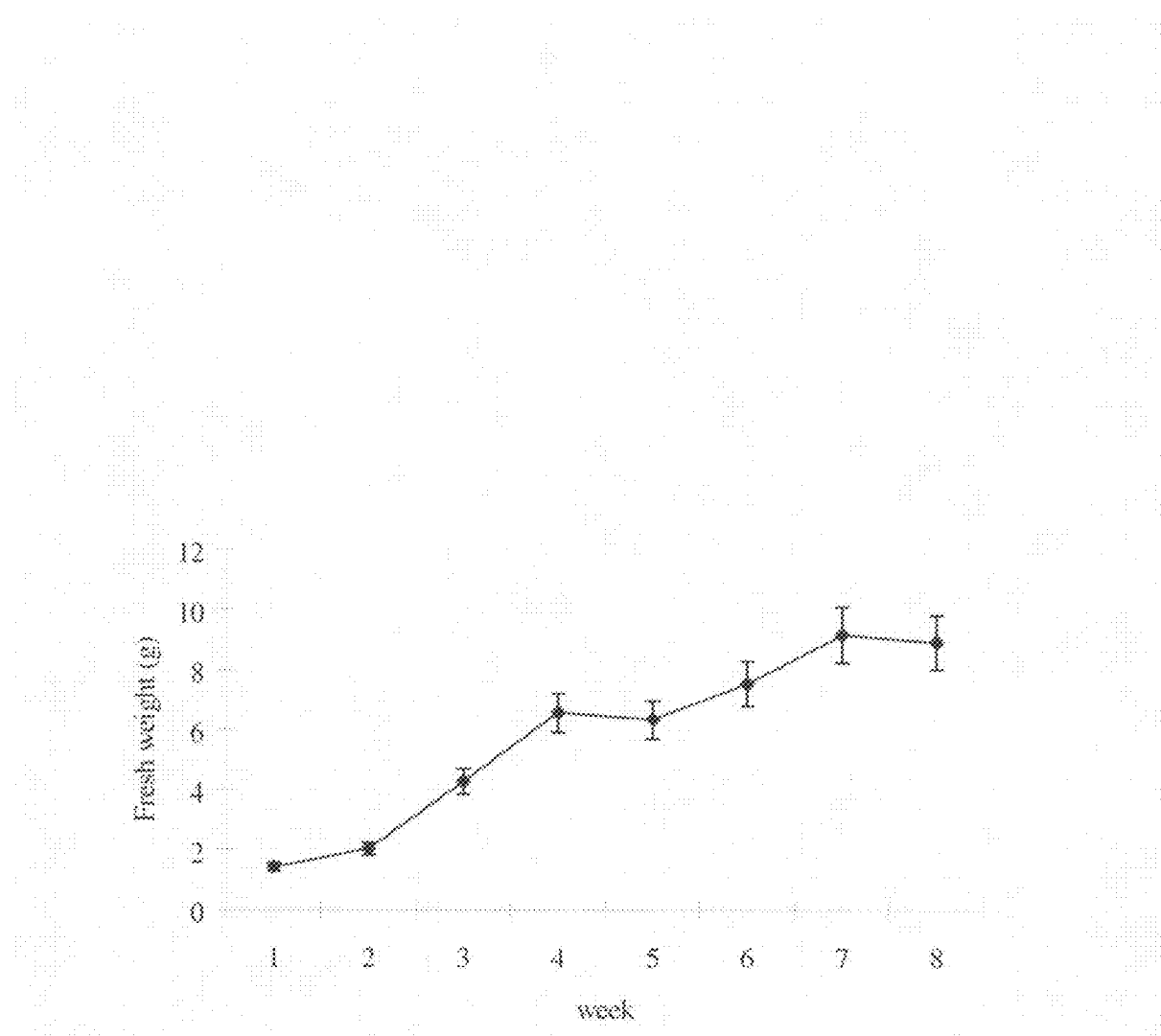
FIG. 4 is a diagram showing the growth curve of *N. gracilis* cultured in an MS medium containing 0.1 mg/L (♦) of α-naphthaleneacetic acid (NAA) for 8 weeks. Each data point represents an average of 3 replications and error bars represent the standard errors of the means.

As shown in FIG. 4, rhizome tissue cultured in an MS basic medium supplemented with 0.1 mg/L NAA grew rapidly during the periods of weeks 3-4 and weeks 6-7. There was little growth during week 5 and week 8. Rhizome tissue cultured in the MS basic medium supplemented with 1 mg/l NAA and 1.0 mg/l 2,4-D showed a similar growth curve.

Figure 5:
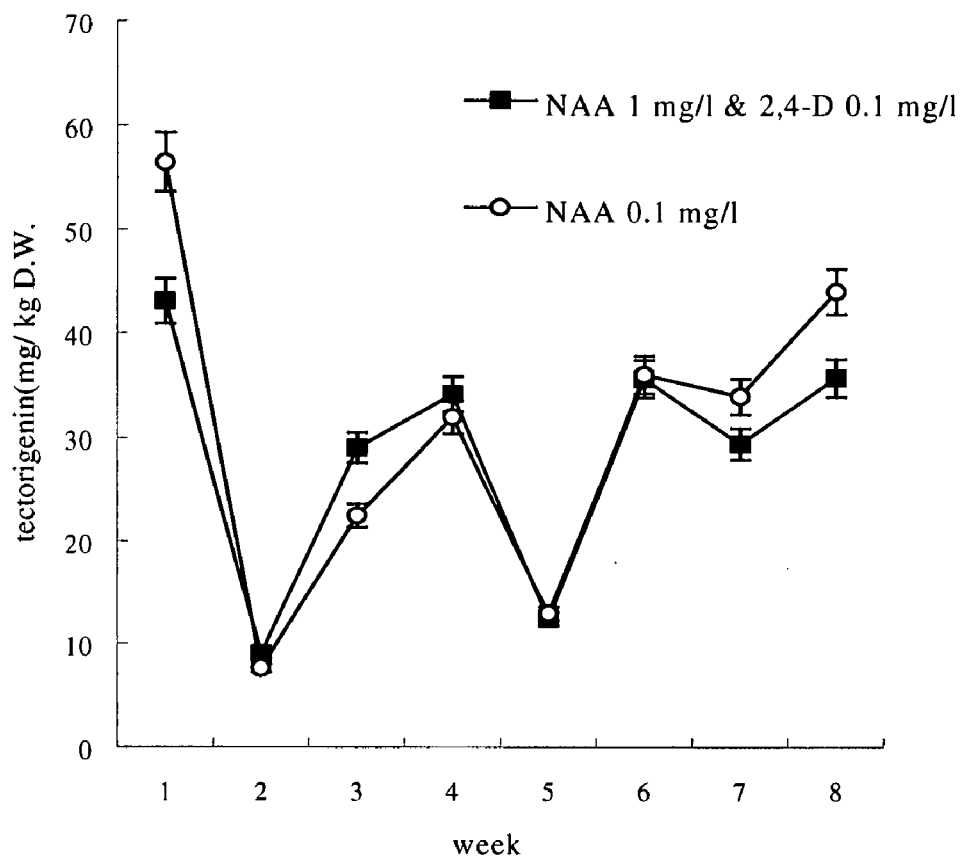
FIG. 5 is a diagram showing the tectorigenin content of the flavonoid-rich rhizome cultured in 0.1 mg/L (○) of MS+NAA, or 1 mg/L of NAA and 0.1 mg/L of 2,4-D (■) for 8 weeks. Each data point represents an average of 3 replications and error bars represent the standard errors of the means.

With regard to the tectorigenin content during growth, the highest content was detected during week 1 under both culture conditions (56±2.82 mg/kg D.W. and 43±2.15 mg/kg D.W. for 0.1 mg/L NAA and 1 mg/L NAA/1.0 mg/L 2,4-D, respectively). The tectorigenin content reduced significantly on week 2, reaching 7±0.42 mg/kg D.W. at the lowest point, and gradually increased over weeks 3-4. The tectorigenin content then showed another significant reduction at week 5 and increased again during weeks 6-8 (FIG. 5).

The total flavonoid content in tissues cultured in MS0 (i.e., MS medium without PGR) in solid culture is generally higher than those in MS in liquid culture medium and in TIS for the same amount of time in culture. The total flavonoid content in solid tissue culture containing MS0 for about 8 weeks was equivalent to about 10.74±0.31 of ψ-tectorigenin mg/g of dry weight, which is similar to the total flavonoid content extracted from the herb of *Belamcanda chinensis*, which is well-known for its high content of flavonoid. The total flavonoid content in *B. chinensis* was about 11.50±0.1 of ψ-tectorigenin mg/g of dry weight based on the same measurement method as used in here.

Example 5

Figure 6:
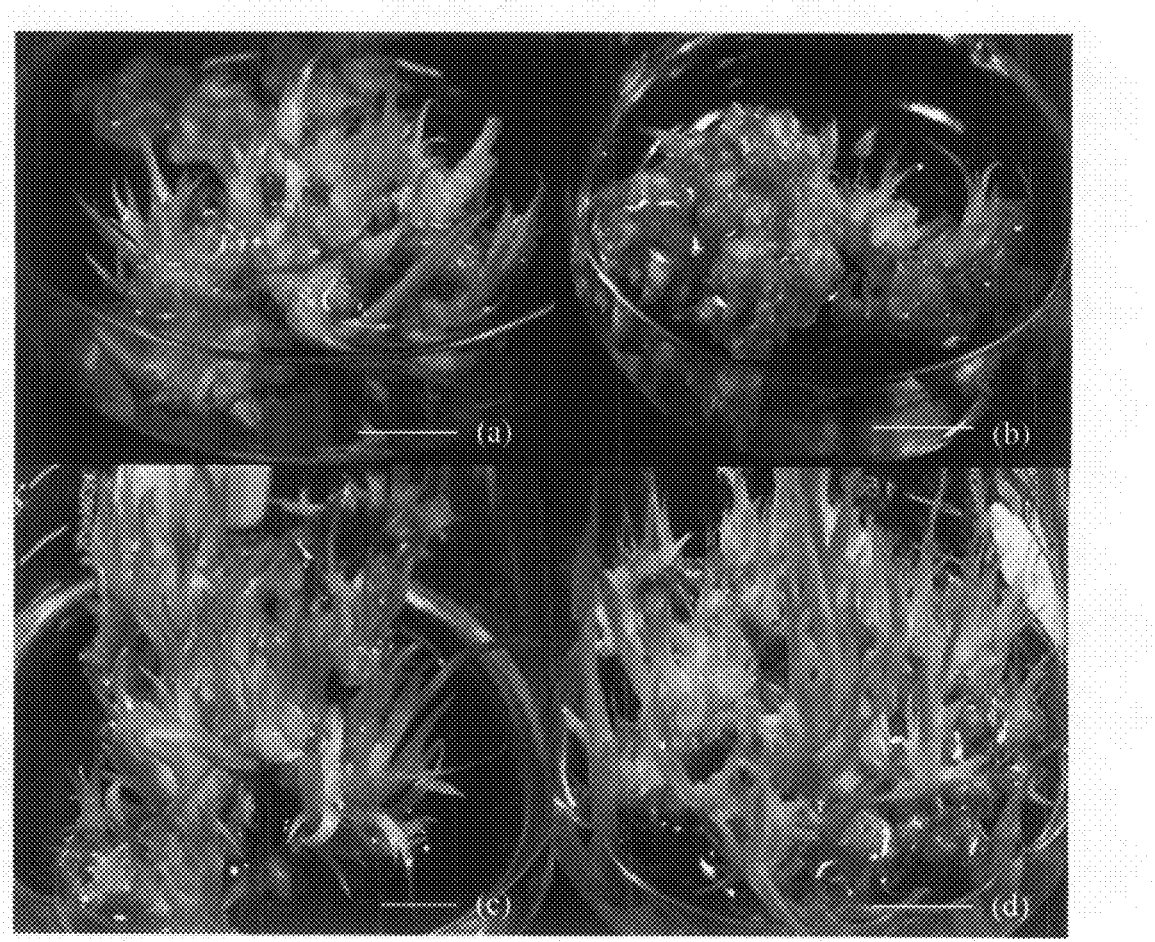
FIG. 6 is a composite of pictures showing sprout formation of *N. gracilis*rhizome tissue in the presence of ancymidol. Photographs were taken after three weeks of culture. Bar=1 cm. Panel (a): 0.5 mg/L ancymidol added on day 7; Panel (b): 2.0 mg/L ancymidol added on day 7; Panel (c): 2.0 mg/L ancymidol added on day 14, and Panel (d) control culture without any ancymidol.

The Effect of Ancymidol on Sprout Formation and Tectorigenin Content of Cultured *N. gracilis* Rhizome Tissues Liquid cultured *N. gracilis* rhizome tissue was inoculated at an inoculum weight of 3% (g F.W./100 ml) to a subculture medium containing MS, 0.5 mg/L BA, 0.1 mg/L 2,4-D and 0.84 mg/L NAA. At day 7 and 14 of the culture, sterilely filtered (0.2 um) ancymidol was added to the culture medium to a final concentration of 0.5, 1.0, or 2.0 mg/L. The growth of the tissue was monitored and the tectorigenin content analyzed. As shown in Table 6, adding 0.5 or 2.0 mg/L ancymidol to the tissue culture on day 14 resulted in reduced tectorigenin content. Adding ancymidol to the tissue culture on day 7 did not affect the tectorigenin content. Morphologically, however, adding ancymidol to the tissue culture on day 7 led to significant reduction of sprout formation (FIG. 6).

TABLE 6

Effect of ancymidol on the tectorigenin content of *N. gracilis* rhizome tissue

| Ancymidol (mg/L) | Adding time (day) | Tectorigenin[1] (mg/kg D.W.) |
|---|---|---|
| Control | — | 32.81 ± 0.72 ab[2] |
| 0.5 | 7 | 28.31 ± 0.11 b |
| 1.0 | 7 | 27.74 ± 0.08 b |
| 2.0 | 7 | 35.65 ± 0.18 a |
| 0.5 | 14 | 18.59 ± 0.07 c |
| 1.0 | 14 | 30.81 ± 0.35 a |
| 2.0 | 14 | 13.36 ± 0.13 d |

[1]Data were collected after 3 weeks of culture. Values are means of 3 replicates ± S.E.
[2]Means within a column followed by the same (a to d) letters are not significantly different by Duncan's multiple range test (P > 0.05).

Example 6

Effect of Inoculum to Biomass Increase of *N. gracilis*

Figure 7:
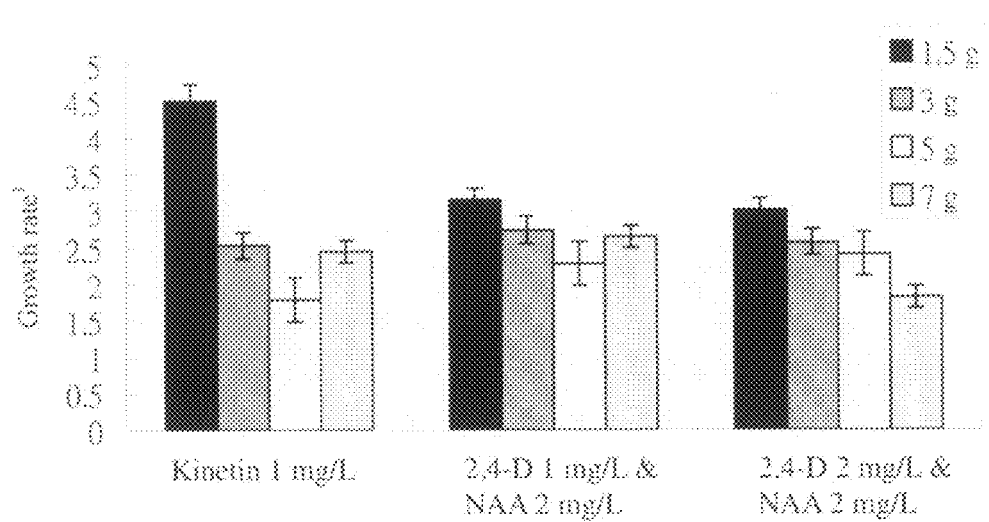
FIG. 7 is a diagram showing the effect of inoculum weight and the plant growth regulators (PGRs) on the growth rate of *N. gracilis* rhizome tissue. Each data point represents the average of 3 replications and error bars represent the standard errors of the means. The growth rate=(Final F.W.–Initial F.W.)/Initial F.W.

The TIS culture chamber was divided into four areas and liquid cultured *N. gracilis* rhizome tissue was inoculated at an inoculum weight of 1.5, 3, 6 and 9 g in each area. The culture medium was MS medium supplemented with PGR as described in samples TI2, TI7 and TI8 of Table 3. The cultured tissue was weighted every ten days. As shown in FIG. 7, the inoculum weight of 1.5 g in MS medium supplemented with 1 mg/L kinetin provided the best tissue growth—reaching a fresh weight (6.76±0.33 g) that was 4.5 fold of the inoculum weight in 30 days. All other inoculum weights/PGR combinations led to slower growth (FIG. 7).

To determine the effect of PGRs on the tectorigenin content, ten pieces of liquid cultured *N. gracilis* rhizome tissue (1.5 g each) were inoculated in culture media containing MS and PGRs described in samples MS0, TI3, TI4, TI5 and TI6 of Table 3. The tissues were harvested on week 4 and analyzed for tectorigenin content. As shown in Table 7, the highest tectorigenin content (48±0.22 mg/kg D.W.) was obtained with MS medium supplemented with 0.1 mg/L 2,4-D and 1.0 mg/L NAA.

TABLE 7

Effect of PRGs on the growth and tectorigenin content of *N. gracilis* rhizome tissue in TIS culture

| PGRs (mg/l) | F.W.(g) | Growth rate[1] | Tectorigenin (mg/kg D.W.) |
|---|---|---|---|
| Control | 42.63 ± 3.51 | 1.84 ± 0.23 | 22 ± 0.11 |
| Kinetin 1.0 | 46.12 ± 2.18 | 2.07 ± 0.15 | 10 ± 0.15 |
| NAA 0.1 | 40.65 ± 2.09 | 1.71 ± 0.14 | 38 ± 0.57 |
| NAA 0.5 | 31.47 ± 3.12 | 1.10 ± 0.21 | 33 ± 0.38 |
| NAA 1.0 + 2,4-D 0.1 | 30.84 ± 1.13 | 1.06 ± 0.08 | 48 ± 0.22 |
| 0.5 BA + 0.1 2,4-D + 0.84 NAA | 33.50 ± 1.03 | 1.23 ± 0.07 | 40 ± 0.52 |

Values are means of 3 replications ± S.E.
[1]Growth rate = (Final F.W. − Initial F.W.)/Initial F.W.

Example 7

Comparision of Tectorigenin Content in *N. gracilis* Rhizome Tissues Cultured in Flask and in TIS Based on the result of Example 2, the combination of 2,4-D and NAA provides higher tectorigenin content than the combination of IAA and Kinetin. The highest tectorigenin contents were obtained by MS medium supplemented with 0.1 mg/L NAA (tectorigenin 55.5±0.67 mg/kg D.W.) 0.5 mg/L NAA (tectorigenin 59.9±0.23 mg/kg D.W.) or 0.1 mg/L NAA and 1 mg/L 2,4-D (tectorigenin 60.9±0.67 mg/kg D.W.) The total flavonoids contents were also determined under these culture conditions.

Example 8

Comparision of Tectorigenin Contents in Cultured and Wild *N. gracilis* Rhizome Tissues Table 8 shows the tectorigenin content in cultured and wild *N. gracilis* rhizome tissues. The results show that wild *N. gracilis* rhizome tissues had no tectorigenin but the cultured *N. gracilis* rhizome tissues had a tectorigenin content of 55.5±0.67 mg/kg D.W.

TABLE 8

The tectorigenin content of cultured and wild *N. gracilis* rhizome tissues

|  | Tectorigenin (mg/kg D.W.)[2] |
|---|---|
| Flask Cultured Rhizome[1] | 55.5 ± 0.67 |
| Wild Rhizome | ND[3] |

[1]The rhizome culture medium was MS with 0.1 mg/l NAA.
[2]Values are means of 3 replicates ± S.E.
[3]ND = not detectable

Example 9

Extract from Cultured *N. gracilis* Rhizome Tissue Inhibits Tumor Cell Growth Extract of the cultured *N. gracilis* rhizome tissue, obtained using the procedure described in Materials and Methods, was tested in vitro in cultured tumor cells. The extract showed no toxicity to human normal intestine cells in the concentration range of 0.1% to 20%. The extract, however, inhibits the growth of mouse melanoma cells (B16-F0) at concentrations of 3.13%, 25% and 50%. The extract was also tested on acute myeloid leukemia cell line PLB985 and human breast cancer cell line MCF7 using lucigenin analysis to monitor the formation of peroxide, followed with analysis of free-radicals by an anti-oxidant analyzer. The result indicated that the extract inhibited the growth of the two tumor cell lines.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. An in vitro cultured tissue from *Neomarica gracilis* (*N. gracilis*), wherein said cultured tissue comprises tectorigenin in an amount detectable by high pressure liquid chromatography (HPLC).

2. The in vitro cultured tissue from *N. gracilis* according to claim 1, wherein said in vitro cultured tissue is a rhizome tissue cultured from an N. gracilis tissue capable of proliferating.

3. The in vitro cultured tissue from *N. gracilis* according to claim 2, wherein said *N. gracilis* tissue comprises root, rhizome, leaf, and a basal portion of leaf.

4. The in vitro cultured tissue from *N. gracilis* according to claim 1, wherein said tissue is cultured in a culture medium which contains a plant growth regulator.

5. The in vitro cultured tissue from *N. gracilis* according to claim 4, wherein said plant growth regulator comprises cytokinins or auxins.

6. The in vitro cultured tissue from *N. gracilis* according to claim 5, wherein said plant growth regulators are at least one selected from the group consisting of indole-3-acetic acid, 2-4-dichlorophenoxyacetic acid, α-naphthaleneacetic acid, 6-benzyl-aminopurine, and kinetin.

7. The in vitro cultured tissue from *N. gracilis* according to claim 4, wherein said plant growth regulator is at a concentration of about 0.01 to 2.0 mg/L.

8. The in vitro cultured tissue from *N. gracilis* according to claim 4, wherein said culture medium further comprises a Murashige and Skoog basic salt medium (MS medium).

9. The in vitro cultured tissue from *N. gracilis* according to claim 8, wherein said MS medium comprises sodium, potassium, nitrate, ammonium, magnesium, sulfate, calcium, iron, chloride, phosphate, manganese, iodine, borate, zinc, copper, molybdenum, cobalt, or a mixture thereof.

10. The in vitro cultured tissue from *N. gracilis* according to claim 4, wherein said culture medium further comprises a carbohydrate.

11. The in vitro cultured tissue from *N. gracilis* according to claim 10, wherein said carbohydrate is myo-inositol or sucrose or a mixture thereof.

12. The in vitro cultured tissue from *N. gracilis* according to claim 4, wherein said culture medium further comprises a vitamin.

13. The in vitro cultured tissue from *N. gracilis* according to claim 12, wherein said vitamin is at least one selected from the group consisting of thiamine HCl, pyridoxine HCl, and nicotinic acid.

14. The in vitro cultured tissue from *N. gracilis* according to claim 4, wherein said culture medium further comprises an ancymidol.

15. The in vitro cultured tissue from *N. gracilis* according to claim 4, wherein said culture medium has a pH of about 5 to 7.

16. The in vitro cultured tissue from *N. gracilis* according to claim 1, wherein said tissue culture preparation is a flask culture, a Temporary Immersion System (TIS), or a combination thereof.

17. The in vitro cultured tissue from *N. gracilis* according to claim 1, wherein said tectorigenin is in the amount of about 2.5 to 65 mg per Kg of dry tissue weight.

* * * * *